(12) United States Patent
Costa Perez et al.

(10) Patent No.: US 8,859,228 B2
(45) Date of Patent: Oct. 14, 2014

(54) METHOD FOR THE PRODUCTION OF BETA-CAROTENE

(75) Inventors: Javier Costa Perez, León (ES); Antonio Estrella Castro, León (ES); Ana Teresa Marcos Rodriguez, Murcia (ES); J. Emiliano Gonzalez De Prado, León (ES); Enrique R. Peiro Cezon, León (ES); Alfonso Collados De La Vieja, León (ES); Manuel Esteban Morales, Murcia (ES)

(73) Assignee: DSM IP Assets B.V., Heerlen (NL)

( * ) Notice: Subject to any disclaimer, the term of this patent is extended or adjusted under 35 U.S.C. 154(b) by 1661 days.

(21) Appl. No.: 10/333,331

(22) PCT Filed: Jul. 18, 2001

(86) PCT No.: PCT/ES01/00284
§ 371 (c)(1),
(2), (4) Date: Nov. 6, 2003

(87) PCT Pub. No.: WO02/10429
PCT Pub. Date: Feb. 7, 2002

(65) Prior Publication Data
US 2004/0067550 A1    Apr. 8, 2004

(51) Int. Cl.
*C12N 1/00*  (2006.01)
*C12N 1/38*  (2006.01)
*C12P 1/02*  (2006.01)
*C12P 23/00*  (2006.01)
*A23L 1/275*  (2006.01)
*C09B 61/00*  (2006.01)

(52) U.S. Cl.
CPC ............... *A23L 1/2753* (2013.01); *C12P 23/00* (2013.01); *C09B 61/00* (2013.01); *Y10S 435/911* (2013.01); *Y10S 435/931* (2013.01)
USPC .......... 435/67; 435/171; 435/244; 435/254.1; 435/256.8; 435/911; 435/931

(58) Field of Classification Search
None
See application file for complete search history.

(56) References Cited

U.S. PATENT DOCUMENTS

| | | | |
|---|---|---|---|
| 2,959,521 A * | 11/1960 | Zajic | 435/67 |
| 3,268,606 A | 8/1966 | Jaeger | |
| 5,130,242 A * | 7/1992 | Barclay | 435/134 |
| 5,364,563 A * | 11/1994 | Cathrein et al. | 516/53 |
| 5,422,247 A | 6/1995 | Finkelstein et al. | |
| 5,466,599 A * | 11/1995 | Jacobson et al. | 435/255.1 |
| 5,714,658 A | 2/1998 | Heidlas et al. | |
| 5,789,647 A * | 8/1998 | Heidlas et al. | 585/833 |
| 6,048,846 A * | 4/2000 | Cochran | 514/168 |
| 6,262,284 B1 * | 7/2001 | Khachik | 554/14 |
| 6,309,677 B1 * | 10/2001 | Gorenbein et al. | 424/764 |

FOREIGN PATENT DOCUMENTS

| WO | WO 91/18108 | * 11/1991 |
|---|---|---|
| WO | 98/03480 | 1/1998 |
| WO | WO98/03480 | * 1/1998 |
| WO | 98/50574 | 11/1998 |

* cited by examiner

*Primary Examiner* — Debbie K Ware
(74) *Attorney, Agent, or Firm* — Ladas & Parry LLP

(57) ABSTRACT

The invention relates to a novel method for the production of β-carotene from submerged cultures of mucoral fungi such as Blakeslea, Choanephora or Phycomyces by adding lectin to the culture medium and performing pH control once fermentation has started. The method involves β-carotene recovery stage that makes it possible to simplify the process, optimize yields and increase purification of the product.

20 Claims, 1 Drawing Sheet

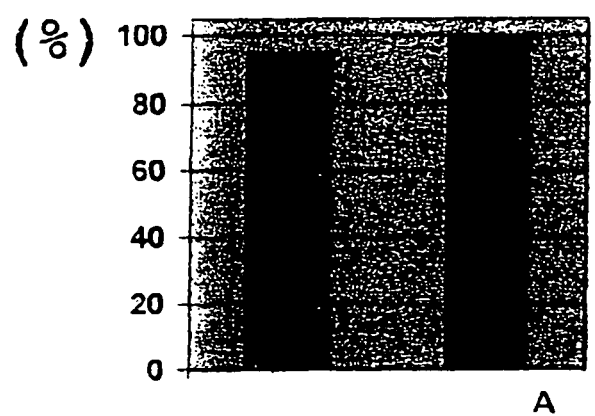
A
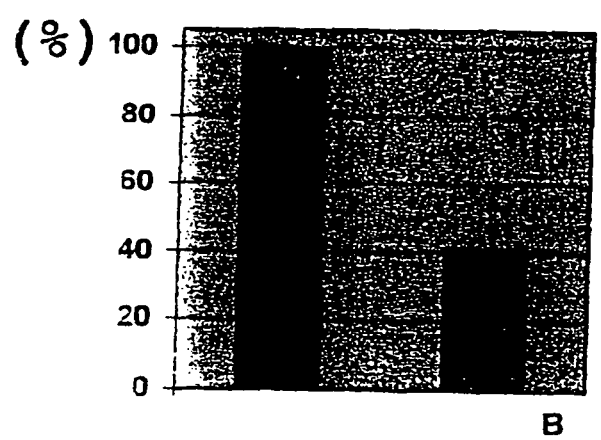
B

METHOD FOR THE PRODUCTION OF BETA-CAROTENE

FIELD OF THE INVENTION

The present invention relates to a new process for the production of carotenoids, in particular β-carotene, from submerged cultures of mucor fungi of the *Blakeslea* genus. A method of fermentation is disclosed that allows an increase in the production of β-carotene to be attained and the relative concentration of this with respect to other carotenoids, based in the incorporation into the culture medium of soy lecithin as well as a defined pH control strategy during fermentation.

Similarly, the present invention discloses an optimised process for the purification and isolation of crystalline β-carotene of high purity from the fermentation broth previously obtained, by means of a simplification of the purification process and an increase in the recovery yield using solvents considered as "natural" and or those included in class III of the ICH (International Conference of Harmonization).

STATE OF THE ART

The carotenoids are abundant compounds in vegetables, the main source from which they were obtained. They have been the object of numerous studies due to their properties as anti-oxidants and as precursors of vitamin A. They represent the most extended group of natural pigments that exists in nature. They are used in industry as a food supplement and colorant in margarines, oils, sauces, soups, etc. (Ninet L. and Renaut J., 1979. In: Peppler H J., Perlman D. (eds). Microbial Technology, $2^{nd}$ edn, vol. 1. Academic Press. NY, pages 529-544).

The carotenoids are isoprenoids that contain a characteristic polyene chain of conjugated double bonds, originating from a condensation of two geranylgeranyl precursors (Pfander (1992). Meth. Enzimol.). There are two groups of pigments: carotenes and their oxygenated derivatives, the xanthophylls.

The empirical molecular formula of β-carotene is $C_{40}H_{56}$, with a molecular weight of 536.85 and the following displayed formula:

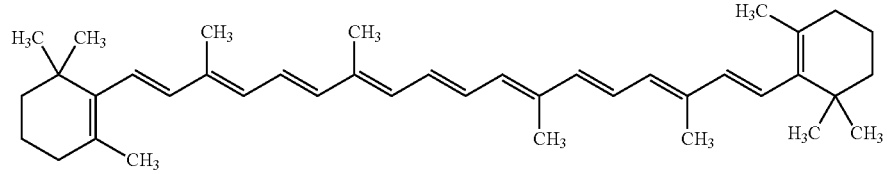 [SMILES: CC1=C(/C=C/C(C)=C/C=C/C(C)=C/C=C/C=C(C)/C=C/C=C(C)/C=C/C2=C(C)CCCC2(C)C)C(C)(C)CCC1]

Trans Beta Carotene

Production of β-carotene as a compound of high purity has been bound to the reaction of classical chemical synthesis, in processes which today are the object of controversy as it is considered that alternative pathways starting from natural sources by fermentation or natural products in conjunction with extraction processes using less drastic solvents and reaction conditions are more advantageous.

Carotenoids and other terpene derivative components in general and β-carotene in particular can be obtained from natural sources, whether vegetal products such as tomato and carrot, in which there are very small percentages or starting from cultures of selected algae, fungi, etc., in which proportion of these components may increase.

Processes for obtaining oleoresins rich in carotenoids and in β-carotene from vegetables, oils or algae are described in various patents.

In most cases, the processes of extraction described require a stage of grinding/extrusion of the fruit to facilitate the extraction of the solvent and to release the intracellular content rich in β-carotene.

The extraction process for these components should address the relatively low concentration and their particular congregation into intracellular agglomerates. As a result, the extraction of β-carotene requires suitable methods that allow the product to be solubilised, either through penetration of the cell walls or by previous rupture of the cell walls, releasing the intracellular content.

The processes described in U.S. Pat. No. 3,268,606, U.S. Pat. No. 2,959,522 use halogenated solvents such as dichloromethane, chloroform, etc., or aromatic hydrocarbons: benzene, toluene, etc., which have problems of inherent toxicity, and which means that they are included in groups I and II of the guide for residual solvents of use in pharmaceutical or food application and according to which it is recommendable to use those that belong to the Class III group.

Most of the methods for extraction of β-carotene from algae use oils. These methods are not suitable for obtaining β-carotene in crystalline form, but rather for obtaining oleic extracts, such as those described in U.S. Pat. Nos. 4,680,314, 4,713,398, 5,019,668, 5,378,369 in which the β-carotene is solubilised and marketed as such.

The use of supercritical $CO_2$ is limited by low solubility of β-carotene. The use of other solvents at pressure in supercritical conditions or as liquefied gases has been considered. Examples include propane or ethylene in which the solubility is greater. Nevertheless, the use of these hydrocarbon solvents would make the use of β-carotene more difficult in the food industry.

Alternatively, β-carotene can be obtained from fermentation broths of certain mucor fungi such as Phycomyces, Blakeslea, etc., which have the advantage over the aforementioned natural sources of the elevated concentration of this compound with respect to the quantity of dry biomass as well as the possible increase in production using super-producing strains obtained by classic mutagenesis techniques or by molecular biology or by means of optimisation of the fermentation process using complex raw materials, certain inducers of production or inhibitors of the production of other structurally related carotenoids that avoid the production thereof.

In any of the methods of production of β-carotene with the fungus *B. trispora*, mixed cultures are used because much higher yields of β-carotene than those of the strains (+) and (−) are obtained than when single cultures are employed (Ciegler, A. 1965). Advan. Appl. Microbiol. 7: 19) and U.S. Pat. No. 5,422,247.

Citric flours have been added to the fermentation medium of β-carotene as a substitute for β-ionone, a chemical stimulant of the biosynthetic pathway [Ciegler, A. 1965. Adv. Appl.

Microbiol. 7, 1-34]. The addition of citric derivatives previously treated with alkali allowed the content of β-carotene to be increased to 1.7 g/l [Upjohn Co., 1965. Dutch Patent 65/00,788].

An analytical study aimed at identifying the stimulating factor or factors of production of β-carotene, contained in citric flours, revealed that citric acid is the main component in addition to a small quantity of malic acid, as well as a third unidentified acid, whose Rf is similar to gluconic acid or to 2-ketogluconic acid. This study concluded that the function of citric acid in the increase in the production is not specific and could act as a precursor of early metabolites in the biosynthetic pathway. In addition, 42% of carbohydrates were found, of which 50% were sucrose and the rest reducing sugars (glucose and fructose) [Pazola Z., Ciegler A., Hall H. H. 1996. Nature 5043:1367-1368].

The lecithins are compounds with a glycerophosphatidylcholine structure, and are present in all living organisms (plants and animals), and are significant constituents of nerve and brain tissue. They are colourless substances, oily to the touch, which melt at around 60° C. and decompose on heating shortly after passing 100° C. The lecithin molecule consists of a mixture of di-glycerides of stearic acid, palmitic acid and oleic acid, bound to the choline ester of phosphoric acid. As the molecule has a dipolar nature, it is extensively used as a surfactant and edible emulsifying agent, of natural origin, with application in the general food industry (chocolate, margarine, etc.), dietetics, pharmaceutical industry and cosmetic industry [Furia, T. E. (ed). CRC Handbook of Food Additives. $2^{nd}$ Ed. Cleveland: The Chemical Rubber Co., 1972. 879]. Commercially available lecithin comes mainly from soybeans, obtained as a by-product in the manufacture of soybean oil although it can also be obtained from sweet corn and other vegetable seeds [Hawley, G. G. The Condensed Chemical Dictionary. $9^{th}$ Edition. New York: Van Nostrand Reinhold Co., 1977. 509]. Soy lecithin contains 11.7% palmitic acid, 4% stearic acid, 8.6% palmitoleic acid, 9.8% oleic acid, 55% linoleic acid, 4% linolenic acid, C20-C22 acids (including arachidonic acid) 5.5% [The Merck Index. $9^{th}$ Ed. Rahway, N.J.: Merck & Co., Inc., 1976. 712].

The effect of soy lecithin on the fermentation has been studied mainly in relation to its use in feeds as a phospholipid supplement and the effect on the fermentation of rumen, with effect on the digestibility of fats and serum triglyceride and cholesterol levels in calves and sheep (Jenkins T C, Jiménez T and Cross D I (1989) "Influence of phospholipids on ruminal fermentation in vitro and on nutrient digestion and serum lipids in sheep" *J. Anim Sci* 67(2): 529-537; Jenkins T C and Fotouhi N (1990) "Effects of lecithin and corn oil on site of digestion, ruminal fermentation and microbial protein synthesis in sheep" *J. Anim. Sci.* 68(2): 460-466; Jenkins T C (1990) "Nutrient digestion, ruminal fermentation and plasma lipids in steers fed combinations of hydrogenated fat and lecithin" *J. Dairy Sci.* 73(10): 2934-2939) as well as on the production of milk in cows (Abel-Caines S F, Grant R J and Morrison M (1998) "Effect of soybean hulls, soy lecithin and soapstock mixtures on ruminal fermentation and milk composition in dairy cows" *J. Dairy Sci.* 81(2): 462-470).

In the production of mildiomycin by means of fermentation of Actinomycetes, in some cases an important increase in production was found following the incorporation into the culture medium of components with an N-methyl nature (especially trimethyl-ammonium groups), among others choline, betaine, lecithin, tetramethylammonium, etc., or natural substances rich in these compounds, or even a combination of the both to avoid a possible overdose of other components of the natural substance in question [U.S. Pat. No. 4,334,022].

Other patents developed in the 80s relate to the incorporation of lecithin to favour the fermentation process in fat-free soybean hulls with the aim of improving their ease of processing and digestion [JP 58116648] as well as their activating effect on the culture of microorganisms used in food processing [DE 3546511; EP 0223161]. On the other hand, the emulsifying character of this compound has been taken into account in applications of elimination of oils by microbes [DE 149056] or in the enzymatic treatment of organic waste effluents [EP 0421223] and in the formation of compost from residues with a high fat content [JP 7033570].

In a recent application, lecithin has also been used for improving the culture medium of the fungus *Lagenidium giganteum*, allowing a greater growth and also a greater effectiveness as a biocontrol agent against mosquitoes of the fungus incubated in such conditions [WO 98/58049].

In U.S. Pat. No. 2,959,521 β-carotene is prepared by cultivating *B. trispora* in a nutrient medium containing lecithin as antioxydant thus stimulating β-carotene production.

In the production of β-carotene by fermentation of *Blakeslea trispora*, the use of some surfactant agents has been described (such as Span 20, sorbitan monolaurate, SIGMA) to increase production through allowing a disperse growth of the mycelium (Seon-Won Kim, Weon-Taek Seo and Young-Hoon Park (1997) "Enhanced production of β-carotene from *Blakeslea trispora* with Span 20" *Biotechnology Letters* 19(6): 561-562). However, no effect on the ratio of the content of β-carotene produced with respect to other carotenoids also present in the cultures of *Blakeslea trispora* (γ-carotene, β-zea-carotene, etc.) are described.

The processes for obtaining β-carotene from fermentation broths described up until present generally imply an extraction stage and successive crystallisations and re-crystallisations and even stages of chromatographic purification, which, due to the nature of these substances, requires a high consumption of solvents because of the low solubility of these substances (U.S. Pat. No. 5,310,554; EP 0242148; U.S. Pat. No. 3,369,974, Biochemistry and Molecular Biology International, 39, 1077-1084 (1996)) and often the purities of product attained are excessively low.

In addition, the solvents normally used, dichloromethane, chloroform, hexane, benzene or toluene, make the use of the β-carotene obtained in the food industry difficult due to their toxicity. Although, recently in U.S. Pat. No. 5,714,658 extraction of β-carotene was achieved by a liquid organic extraction agent comprising an acetic acid ester of $C_1$-$C_4$ alcohols.

When the crystals of β-carotene are obtained directly by crystallisation of the organic extract from a fermentation broth through direct evaporation of the solvent, the crystals obtained do not have the necessary purity compared to synthetic β-carotene, and several stages of re-crystallisation and/or purification are required with the subsequent solvent consumption, complexity of the process and losses of product, leading to low recovery yields.

Recently, the preparation of crystals of β-carotene have been described in the patent PCT WO 98/03480 through successive washing with water or alcohols of low molecular weight, starting from an extract of ethyl acetate obtained by extraction of the biomass from a fermentation broth, which although yielding highly pure β-carotene crystals, requires a high consumption of solvents such as ethyl acetate and ethanol, successive stages of washing and crystallisation which give rise to low recovery yields for the product. In WO98/50574 a step of removal of lipids with a lower alcohol, from a biomass of *B. trispora* used for producing β-carotene with 93.9% purity, is disclosed.

SUMMARY OF THE INVENTION

The object of the present invention is to increase the production of β-carotene in a fermentation process with mucor fungi (Blakeslea, Phycomyces, etc.), more specifically *Blakeslea trispora* through the culture of the fungus in a fermentation medium containing variable quantities of lecithin, particularly soy lecithin, applying a defined strategy for control of the pH during the fermentation.

Similarly, in this invention, production of crystalline β-carotene of high purity is described from a fermentation broth, using solvents considered as natural. Natural solvents are those that, on the one hand, are toxicologically innocuous and/or those that are included in class III of the ICH guidelines (International Conference of Harmonization).

In a general consideration, the process comprises the following stages:
0) Fermentation in a culture medium with lecithin and in predetermined conditions of pH control
1) Separation of the wet biomass from the natural source of biosynthesis (the fermentation broth for example)
2) Purification of the wet biomass by treatment with alcohol
3) Separation of the purified biomass from the alcohol
4) Conditioning of the purified biomass through drying and disintegration or rupture thereof
5) Solid-liquid extraction of β-carotenoids with an organic solvent
6) Concentration of the enriched extract
7) Precipitation/crystallisation by addition of alcohol
8) Filtration
9) Drying The method described here allows us to recover crystalline β-carotene with a purity greater than 90%, preferably greater than 95% and more preferably greater than 98%.

BRIEF DESCRIPTION OF THE DRAWINGS

FIG. 1A is a bar graph showing percentage production of β-carotene with lecithin (right column) and without lecithin (left column); and FIG. 1B is a bar graph showing percentage production of γ-carotene with lecithin (right column) and without lecithin (left column).

DETAILED DESCRIPTION OF THE INVENTION

The present invention describes a process for increasing the production of β-carotene in a fermentation process with mucor fungi (Blakeslea, Choanephora or Phymomyces, more specifically *Blakeslea trispora*. The invention consists of culturing the fungus *B. trispora* in a fermentation medium containing by-products derived from the manipulation of citrics, in particular citric flours, which have been obtained by means of a process of elimination of pectins through treatment with calcium hydroxide and successive treatments of change of pH and washing to concentrate certain components that induce the production of β-carotene. Within the citric flours, flours can be used that come, for example, from oranges, grapefruit, mandarin, etc. and within each one of these, the different varieties of each one of them, for example, Navel, Naveline, Clementine, Washington, Valencia-late etc.

On one hand, the invention consists in that the culture medium also contains soy lecithin and on the other hand, on applying a defined strategy for controlling the pH during fermentation. The joint effect of these variables allows an increase in the production of β-carotene and in the relative concentration of this with respect to other minority carotenoids.

The organisms used for the fermentation can be isolated strains (+) or (−) or a mixture of strains (+) and (−) of mucor fungi, more specifically *B. trispora* or else β-carotene super-producing mutants of *B. trispora*. Several mixtures of strains (+) and (−) of the fungus can be used in the fermentation process of the invention.

The fermentation process can be performed in any culture medium containing one or more sources of carbon, one or more sources of nitrogen, mineral salts, thiamine and variable proportions of citric flours from a single citric source and a single variety or mixtures of flours from different citric fruits and/or varieties and soy lecithin in variable proportions that range from 0.1% to 10% and preferably from 0.5% to 5% and more preferably from 0.5% to 1.5%.

The carbon sources that can be used as single or complex nutrients include carbohydrates or fats such as dextrines for example, starches, glucose, sucrose, fructose, animal and vegetable oils. Within the nitrogen sources, organic and inorganic sources can be used such as for example soybean hulls, corn flour, soluble distillates, yeast extract, cotton flour, peptones, casein or ammonium sulphate. The mineral salts that can be added to the culture medium include phosphates, sulphates, chlorides of monovalent cations such as sodium, potassium or ammonium or divalent cations such as calcium or magnesium. The proportions of nutrients are determined as a function of the growth needs of the microorganism and the production levels.

The fermentation is carried out in aerobic conditions and submerged culture. The fermentation temperature ranges from 20° C. to 32° C. although the range between 25° C. and 28° C. is preferred.

The pH of the culture evolves freely in the first hours, in which there is an initial growth of the fungus in the fermenter. The pH is then controlled by means of the addition of acid and/or alkali within the range of 6.5-7.2 although preferably 6.7-6.9. The start of the pH control depends on the evolution of growth, but in general it takes place after between 12 and 50 hours of fermentation, preferably between 24 and 36 hours.

The incorporation of lecithin into the medium, due to the amphipatic character of this molecule favours the emulsion of the oils in the culture media in which these are found in high concentration, as is often the case in fermentation media of β-carotene. This action on the one hand favours the use of the oil by the microorganism and on the other it has surprisingly been found that it activates the carotenogenesis pathway favouring the transformation of gamma-carotene into beta-carotene, increasing the production of this latter substance and its relative concentration with respect to other carotenoids, especially the gamma-carotene, and so it leads to an important reduction in the presence of this substance in the final product, increasing the purity of all-trans beta-carotene.

In addition, this effect is enhanced when a suitable pH control is performed during the fermentation, so that adjusting the pH after 24-36 hours of fermentation favours the reduction of the gamma-carotene in an even more marked fashion, increasing the relative concentration of the beta form.

The presence of gamma-carotene in the fermentation broths of mucor fungi in cultures in stationary phase has been described before (Murillo F J, Torres-Martinez S, Aragon C M and Carda-Olmedo E (1981) "Substrate transfer in carotene biosynthesis in Phycomyces" *Eur. J. Biochem.* 119(3): 511-516; Candau R., Bejarano E R, Carda-Olmedo E (1991) "In vivo channelling of substrates in an enzyme aggregate for beta-carotene biosynthesis" *Proc. Natl. Acad. Sci. USA* 88(11): 4936-4940; Fraser P D, Ruiz-Hidalgo M J, Lopez-Matas M A, Alvarez M I, Eslava A P and Bramley PM (1996) "Carotenoid biosynthesis in wild type and mutant strains of Mucor circinelloides" *Biochim Biophys Acta*1289(2): 203-208).

This presence has also been described in *Blakeslea trispora* (Mehta B J and Carda-Olmedo E (1999) "Lycopene cyclization in *Blakeslea trispora*" *Mycoscience* 40(3) 307-310). In both cases, these inhibitory effects are described for some substances such as nicotine, 2-(4-chlorophenylthio)-triethylamine, alpha-picoline and imidazole on the production of beta-carotene, favouring however the accumulation of lycopene-gamma-carotene due to the blocking of lycopene-cyclase. However, no processes have been described previously aimed at reducing the content of gamma-carotene in the fermentation of *B. trispora* increasing the production of beta-carotene and therefore the purity of the final product obtained.

This effect of reduction of the content of gamma-carotene in the fermentation broths of *Blakeslea trispora* result of the present invention is of importance in the sense that it allows the specifications established both at a Pharmacopoeia level and for the food industry of the final product required a purity of beta-carotene of at least 96% in the final product to be met.

Given the characteristics of the carotenoid component biosynthesised in the fermentation, on being intracellular, the recovery process from the culture broth, prepared in accordance with the current processes, implies the separation of the biomass of the broth with the aim of eliminating or reducing the losses in the broth without biomass.

This separation can be made by the established processes of A) Filtration, using the current filter technologies, either strips, rotary, presses, etc., in which the barrier constituted by the filtering material separates the biomass and allows the liquid to pass without the biomass, or B) Centrifugation, in which, making use of the different densities between the broth and the biomass (usually higher) a machine such as a centrifuge, decanter or similar is used, in which the heavy phase is concentrated and separated from the liquid phase with the lowest possible quantity of biomass. Reducing losses and optimising the yield of each respective phase thus achieving the largest quantity of biomass with the highest content of dry residue and eliminating the greatest quantity from the fermentation broth is one of the objectives of this invention.

The resulting wet mycelium contains more than 95% of carotenoids produced in the fermentation, preferably more than 97% and more preferably more than 99%. The content in carotenoids of the aqueous phase is, therefore, less than 5%, preferably less than 3% and more preferably less than 1%.

This wet solid of mycelium would enable, through subsequent stages, the separation of beta-carotene but the finding that, related to the fermentation, it maintains a relatively high percentage of lipophilic component, between 15 and 20% (fatty acids and oils) and that in subsequent stages purification problems arise, leads to the introduction, due to this point, of a purification stage of the biomass.

This purification stage implies a re-suspension of the biomass with a quantity of alcohol, methanol, ethanol, propanol, isopropanol, or any other alcohol in which the solubility of β-carotene is very low, or mixtures thereof, in suitable proportion to achieve the maximum purification of the lipid components, in other words, the wet mycelium is re-suspended with a quantity of alcohol that ranges from 1 ml/g to 10 ml/g of wet mycelium. The temperature of re-suspension ranges between room temperature and the boiling point for alcohol. The contact time ranges between 5 minutes and 24 hours. The alcohol re-suspension thus prepared is filtered or centrifuged, so that the content of solids in the filtrate or supernatant is practically zero. The resulting wet mycelium, that will contain alcohol and water in different proportions, contains more than 93% of the carotenoids produced in the fermentation, preferably more than 95% and more preferably more than 97%.

In the resulting mixture of remains of broth with alcohol, the content in carotenoids is less than 2%, preferably less than 1%. Through this treatment with alcohol, it is possible to eliminate a series of lipophilic substances soluble in alcohol that vary as a function of the characteristics of the broth used, performing a prior extremely important purification and one which will allow us to obtain a final crystalline product of high purity. In addition, the elimination of a variable proportion of water from the initial wet mycelium considerably facilitates the drying process.

As an alternative to the set of these two stages of separation of the biomass and purification by re-suspension, the possibility is considered of directly mixing the harvested broth with alcohol in proportions of volume between 1:0.5 and 1:5 (broth/alcohol) and at temperatures between room temperature and that of the boiling point of the mixture, preferably between room temperature and 50° C., keeping the minimum contact time a purification effect equivalent to that described is achieved, whereby the process is simplified through the elimination of the operation of solid/liquid separation.

The fact that the carotenoid product is intracellular implies that the purified biomass requires conditioning by drying and grinding, drying and disintegration or only disintegration of the biomass, which favours mixing with solvents and facilitates extraction.

The dehydrated purified mycelium is dried. The drying can be performed using normal processes in solid batches or continuously. The drying temperature ranges from room temperature to 150° C., preferably should not exceed 60° C. and more preferably should be below 50° C. The drying time depends on the temperature used, ranging from 1 hour to 72 hours. Due to the possible decomposition of these carotenoids through oxidation by atmospheric oxygen, it is convenient to perform this drying process in the absence of oxygen, either under nitrogen atmosphere or at least under vacuum.

In order to allow the solvent good access to the carotenoid to be extracted, it is necessary to carry out a prior rupture operation on the mycelium, so that the surface area of contact is maximised. The optimum particle size of the dry and broken mycelium should be less than 3 mm, preferably less than 1 mm and more preferably less than 0.5 mm.

The biomass disintegration can be carried out on the dry product by conventional means, for example by using mechanical grinding means with rotating or fixed parts: pestles, sieves, etc., by passing through rotating cylinders pressing against one another or by a flash-type drying in the jet-mill equipment where the wet product is fed to a current of circulating gas at a high temperature, such that the residence time is minimised in order to achieve vaporisation of the content of the liquid components, and it is transported, due to differences in the densities of the product, to a cyclone where it is recovered.

During the drying time and its travel there is a homogenisation effect as the particles collide with the walls.

For the extraction of β-carotene from mycelium conditioned as described here, different organic solvents can be used. This invention relates to the use of food-grade solvents considered as natural, such as acyl esters, preferably ethyl, propyl, isopropyl, butyl, isobutyl esters, or mixtures thereof which combine reasonably high solubility for the carotenoid components with their compatibility as solvents included in the Group of Class III of the ICH. These solvents are admissible both in Spain and within the European Community, for both pharmaceutical and food applications (RDL 12/04/96 and RDL 16/10/96).

The extraction temperature varies between room temperature and that of the boiling point of the solvent, preferably between 50° C. and 80° C. The extraction time will be the minimum necessary to achieve solubilisation, between 1 second and 1 hour, preferably between 1 minute and 15 minutes. The quantity of solvent used depends on the temperature and the richness of the mycelium in carotenoids, ranging between 5 ml/g and 20 ml/g. The number of extractions varies from 1 to 3. The quantity of carotenoids extracted is greater than 85%, preferably greater than 90% and more preferably greater than 95%.

Once the extract rich in carotenoids has been obtained it is necessary to concentrate it to a certain volume. The final concentration of carotenoids in the solvent after concentration varies preferably between 10 and 40 g/l. The concentration temperature should be less than 80° C., preferably less than 70° C. and more preferably less than 50° C. The concentration time should be less than 1 hour, preferably less than 30 minutes, and more preferably less than 15 minutes.

Once the extract has been concentrated to the required volume, it is necessary to add a carotenoid insolubiliser, specifically an alcohol and more specifically anhydrous methanol, ethanol, isopropanol, or any other alcohol in which the solubility of β-carotene is low, in proportions between 1/1 and 6/1 with respect to the volume of solvent after concentration, by which the yield of crystalline β-carotene increases considerably. The addition of the alcohol also has a purifying effect, recovering a purer product than when it is not added. The crystallisation time varies between 15 minutes and 24 hours, preferably between 1 hour and 12 hours and more preferably between 3 and 8 hours. The crystallisation temperature should be less than 25° C., preferably less than 5° C.

The separation of the crystals from the waters of crystallisation can be performed by filtration or centrifugation, displacing the waters of crystallisation that bathe the crystals washing them with the same alcohol used to insolubilise them.

The crystals obtained are dried under vacuum at room temperature for at least 1 hour until a residual content of solvent in accordance with the specifications of maximum concentration established by legislation is attained and in the case of β-carotene, a loss on drying of <0.2% is established.

The beta-carotene purity of the crystals obtained corresponds to a titre determined by spectrophotometry by reading the absorption at 455 nm dissolved in cyclohexane (E1% 1 cm=2500) according to the spectrophotometric method of the USP, EP, BP, greater than 90%, preferably greater than 95% and more preferably greater than 98% with a content in other carotenoids less than 4%, preferably less than 2%.

Similarly the crystalline product obtained can be handled and marketed as such or forming part of formulations in which the proportion of β-carotene varies between 1 and 85%, mixing with different excipients or compounds, such as soybean oil, corn oil, olive oil, etc., with different degrees of purity and accompanied by an anti-oxidant of the tocopherol type. An object of the present invention is to provide a formulation of carotenoids dispersible in water, which contains approximately 1 to 25 parts by weight of dry powder of carotenoids encapsulated in a starch matrix of food quality that provides β-carotene included in the powder encapsulated in a stable condition. Different types of starch may be used.

The product of the present invention are solid formulations of β-carotene, dispersible in water.

The preferred starches used are modified cornstarches of food quality with a high molecular weight, which allows a simple emulsification of the organic phase in water. After separating the solvent, the dispersion satisfies the range of colours of β-carotene. This modified food starch does not produce sufficient re-dispersibility of the dry powder. Thus, another starch is also added. The second variety is a mixture of starches of food quality of different molecular weights in a range of 1,000-700,000; this second type of starch provides a good dispersibility of the final product.

As β-carotene is sensitive to oxidation, antioxidants can be dissolved in the solvent containing the β-carotene to intensify the stability against deterioration. In the present invention, any antioxidant authorised in foods can be used, including among others, α-tocopherol of natural or synthetic origin. The antioxidant level will be sufficient to protect the β-carotene. This must be 0.1 to 0.3 the amount of β-carotene. Ascorbyl palmitate can also be added to the formulation due to the synergic antioxidant effect of the association of the two antioxidants.

The method of this invention is especially applicable for the recovery of crystalline β-carotene from a microbial source, preferably algae, fungi or yeasts, more preferably from fungi of the Mucor order, and more preferably from *B. trispora*.

The extreme purity attained in the crystals obtained by the present methodology and the use of solvents considered as natural means that these crystals are applicable in the food industry, pharmaceutical industry or cosmetics industry.

EXAMPLE 1

The addition of soy lecithin to the culture medium reduces the content of gamma-carotene when it is fermented in a flask.

An inoculum medium is prepared that contains per liter: soybean hulls, 23 g; corn flour, 47 g; monopotassium phosphate, 0.5 g; thiamine hydrochloride, 0.002 g. Its initial pH is 6.3. The medium is distributed in 500 ml Erlenmeyer flasks at either 67 or 100 ml. After sterilisation, they are seeded with suspensions of spores of *B. trispora* strain (+) and *B. trispora* strain (−) in separated flasks and incubated at 25° C. for 48 hours.

The base fermentation medium is prepared that contains per liter: soybean hulls, 44 g; corn flour, 19 g; orange flour, 10 g; thiamine hydrochloride, 0.002 g; vegetable oil 100 g. The culture medium that contains soy lecithin is prepared according to the previous description and supplemented with 1% lecithin. The pH is adjusted to 6.3. The medium is distributed in 250 ml Erlenmeyer flasks in portions of 20 ml.

For the fermentation of β-carotene, the flasks that contain the fermentation medium are inoculated with 10% of mixed culture of strains of *B. trispora* (+) and *B. trispora* (−). All flasks are incubated at 25° C. in an orbital shaker at 250 rpm. After 48 hours of fermentation, β-ionone is added to the flasks at a ratio of 1 ml per liter of culture medium and the mycelium is collected on the $6^{th}$ day of fermentation.

The extraction of β-carotene is carried out using any described method of cell rupture that allows the intracellular content to be released. It is solubilised in any solvent in which it is soluble such as acetone for example. Its concentration can be assessed by means of spectrophotometry but the use of liquid chromatography is preferred (HPLC), using any of the methods described in the literature.

The addition of soy lecithin increases the production of β-carotene by 5% and reduces the production of γ-carotene by 60% (see FIG. 1). This experiment shows that lecithin allows the production of β-carotene to be increased and also helps the production of a purer product.

EXAMPLE 2

The incorporation of lecithin into the culture medium increases the production of beta-carotene and reduces the relative level of gamma-carotene in a pilot fermenter. When it is combined with the control of pH, the effect on the production of gamma-carotene is even greater.

An inoculum medium is prepared that contains per liter: soybean hulls, 23 g; corn flour, 47 g; monopotassium phosphate, 0.5 g; thiamine hydrochloride, 0.002 g. Its initial pH is 6.3. The medium is distributed in 2000 ml Erlenmeyer flasks, with 500 ml in each flask. After sterilisation, they are seeded with suspensions of spores of B. trispora strain (+) and B. trispora strain (−) in separated flasks and incubated at 25° C. for 48 hours with orbital shaking at 250 rpm and 5 cm eccentricity.

Each one of the strains is transferred under sterile conditions to an intermediate growth tank with a culture medium with the following composition per liter: Pharmamedia, 29 g; corn flour, 47 g; monopotassium phosphate 0.5 g; thiamine hydrochloride, 0.002 g; anti-foaming agent, 1 g. Its initial pH is 6.0.

After incubating for 36-48 hours, a mixture of the (+) and (−) strains is made and 10% of the mixture is used to seed the base fermentation medium, whose composition per liter is as follows: soybean hulls, 50 g; corn flour, 25 g; orange flour, 15 g; monopotassium dibasic phosphate 0.5 g; isoniazid, 0.28 g; thiamine hydrochloride, 0.002 g; vegetal oil 80 g, anti-foaming agent, 0.175 g. This culture medium is supplemented with 1% soy lecithin.

The fermentation is verified at a temperature of 25-28°C. with variable stirring between 150 and 250 rpm and an aeration of 1-1.5 v/v/m. The pH control is performed with ammonia or sulphuric acid, keeping two different conditions depending on the test: without control of pH with a range between 6.5 and 7.5 or with control at 6.8±0.1 after 36 hours of fermentation. Between 40 and 50 hours of fermentation, 10 g/L of a 10% solution of β-ionone in vegetal oil are added. Between 50 and 60 hours, 10 g/L of a 2.5% solution of ethoxyquin in vegetal oil are added.

The fermentation is extended for 100-140 hours, after which time the production of β-carotene is assayed: the extraction of β-carotene is performed by any method described with cell rupture that allows the intracellular content to be released. It is solubilised in any solvent in which it is soluble, for example, acetone. Its concentration can be determined by spectrophotometric means, but the use of liquid chromatography (HPLC) is preferred, using any of the methods described in the literature.

The results of the tests performed with the culture medium with and without lecithin and the two pH control conditions mentioned above are presented in the following table:

| CULTURE MEDUIM | pH | BETA-CAROTENE (%) | GAMMA-CAROTENE (% with respect to beta-carotene) |
|---|---|---|---|
| Without lecithin | Range 6.5–7.5 | 100 | 5.6 |
| Without lecithin | Control 6.8 From 38 h onwards | 95 | 3.2 |
| With lecithin | Range | 105 | 4.4 |

| CULTURE MEDUIM | pH | BETA-CAROTENE (%) | GAMMA-CAROTENE (% with respect to beta-carotene) |
|---|---|---|---|
| With lecithin | 6.5–7.5 Control 6.8 From 38 h onwards | 105 | 2.1 |

These data clearly indicate that the incorporation of lecithin to the culture medium increases the production of beta-carotene (5% increase) and reduces the relative level of gamma-carotene (by 43%). When combined with a control of pH, the effect on the production of gamma-carotene is even greater (63%).

EXAMPLE 3

Three liters of fermentation broth are harvested. The titre of the broth is 6 g of β-carotene per liter. The biomass of these broth is recovered by means of a Buchner filtration, obtaining 1000 g of wet biomass. The wet biomass is re-suspended in 3 l of azeotropic isopropanol 85/15 and shaken for 30 minutes. The purified biomass is once again recovered by a Buchner filtration.

This biomass is dried in an oven under vacuum at a temperature less than 45° C. and for 18 hours, until the content of residual solvents is in the range of 1-2%. A total of 270 g of dry biomass are obtained and purified with a β-carotene content equivalent to a purity of 6.5%.

The dry biomass is ground in a hammer mill and 1 mm sieve to give a solid with the same specific purity and conditioned to allow extraction with the solvent.

The extraction is carried out by mixing 270 g of ground biomass with 4500 ml of isobutyl acetate at 70° C., keeping stirring for 5 minutes. The depleted biomass is separated from the rich solvent by filtering through a filter plate. The depleted biomass is washed with 500 ml of warm isobutyl acetate over the filter itself, mixing the two solvents. The total of rich isobutyl acetate is concentrated under vacuum with the temperature kept between 45° C. until the volume is reduced to 700 ml, at which point part of the β-carotene has crystallised. To complete the crystallisation and obtain purer β-carotene, 2100 ml of isopropanol are added. The mixture is kept shaking at between 0 and 5° C. under nitrogen for 3 hours. It is filtered through a Buchner funnel, washing the crystals with 25 ml of isopropanol over the Buchner funnel. The crystals are collected and dried, obtaining 14 g of crystals of β-carotene with a purity of 96% as measured by spectrophotometry.

EXAMPLE 4

Approximately 500 l of fermentation broth are harvested, with a β-carotene titre of approximately 5.5 g/l. This is mixed directly with 1500 l of azeotropic isopropanol with water 85-15 and the mixture is heated to 40° C. After keeping stirring for 30 minutes, the biomass is separated from the liquid by centrifugation with a decanter. Around 180 Kg of purified wet biomass is collected.

This biomass is dried in a rotary drier under vacuum until attaining a residual solvent content in the range of 1-2%. The temperature has to be less than 45° C. and the time in the range of 12-24 h. 45 kg of dry biomass is obtained with a β-carotene content equivalent to a specific richness of 5.9%, a slightly lower purity.

The dry biomass is ground in a hammer mill and 1 mm sieve to give a solid with the same specific purity and conditioned to allow extraction with the solvent.

As an alternative, the wet biomass is dried in a flash turbo drier (jet-mill type) in which case the grinding step is not necessary.

The extraction is performed mixing the 45 kg of ground solid with 800 l of isobutyl acetate at 70° C., maintaining shaking for 15 minutes. The depleted biomass is separated from the rich solvent by centrifugation with decanter. The total of isobutyl acetate is concentrated under vacuum with the temperature kept below 45° C. until the volume has been reduced to 110 l, at which point part of the β-carotene has crystallised. To complete the crystallisation of β-carotene, 330 l of isopropanol are added. The mixture is kept shaking while it cools, for 3 h at 0-5° C. It is filtered through a Buchner funnel collecting the crystals of beta-carotene that are dried. 2.1 kg of product are obtained with a purity of 96% as measured by spectrophotometry.

The invention claimed is:

1. In a process for the production of beta-carotene that comprises the stages of:
   (1) fermentation of a biomass based on mucor fungi as a submerged culture in a culture medium;
   (2) separation of the biomass;
   (3) purification of the biomass by removal of lipophilic components other than carotenoids by means of extraction with alcohol;
   (4) drying the biomass;
   (5) solid/liquid extraction of the carotenoids contained in the biomass with food-grade organic solvents;
   (6) concentration of an extract rich in carotenoids;
   (7) precipitation-crystallization of the carotenoids by means of the addition of alcohol; and
   (8) filtration and final drying to recover crystals comprising the beta carotene;
   the improvement comprising increasing the production of beta-carotene by reducing a content of gamma-carotene in the culture medium with respect to beta-carotene in the culture medium by conducting the fermentation in stage (1) in the presence of a percentage of soy lecithin and, after an initial growth stage in which the pH is allowed to evolve freely, adjusting the pH into the range 6.7-6.9 after fermentation has been proceeding for a period of between 24-36 hours, and thereafter continuing the fermentation, wherein the fermentation of the submerged culture is performed under aerobic conditions at a temperature of from 20 to 32° C., the mucor fungi belongs to the Blakeslea genus and the recovered crystals have a purity of beta-carotene of greater than 95% with a content of other carotenoids of less than 4%, and wherein the percentage of the soy lecithin in the culture medium combined with the adjustment of pH results in a resultant level of gamma-carotene with respect to beta-carotene in the culture medium being less than a level that could be achieved without the adjustment of pH, said resultant level being less than 4.4%.

2. A process according to claim 1, wherein the soy lecithin is present at a percentage of 0.1-10%.

3. A process according to claim 1, wherein the step of purification of the biomass for removal of lipophilic substances consists in suspension of the same in alcohol in which the solubility of the carotenoids is low.

4. A process according to claim 1, wherein the purification of the biomass is carried out in the culture medium itself directly after stage (1) or, alternatively, once separated from said medium.

5. A process according to claim 1, wherein the quantity of alcohol to be added is between 1 ml/g and 10 ml/g of wet mycelium, the temperature during the suspension ranging from room temperature to the boiling point of the added alcohol, the contact time being 5 minutes to 24 hours.

6. A process according to claim 4, wherein when the purification of the biomass occurs on the culture broth directly, the broth:alcohol ratios range from 1:0.5 to 1:5.

7. A process according to claim 1, wherein the drying stage (4) of the biomass is performed in batches or as a continuous process, in the absence of oxygen, at a temperature that ranges from room temperature to 150° C. and for a time ranging from 1 hour to 72 hours.

8. A process according to claim 7, wherein during the drying stage (4), the biomass is broken into particle sizes of less than 3 mm.

9. A process according to claim 1, wherein the alcohol used in the purification of the biomass is selected from methanol, ethanol, propanol or isopropanol, or mixtures thereof.

10. A process according to claim 1, wherein the extraction stage (5) is repeated between 1 and 3 times and consists of washing the dry and disintegrated biomass with organic food-grade solvents, at a temperature between room temperature and the boiling point of the solvent, for a time that ranges from 1 second to 1 hour, in a quantity that ranges from 5 ml/g to 20 ml/g, obtaining an extract rich in carotenoids with a content of the carotenoids being greater than 85%.

11. A process according to claim 1, wherein the solvent used in extraction stage (5) consists of an acyl ester.

12. A process according to claim 1, wherein the extract rich in carotenoids is subjected to a concentration stage (6) at a temperature of less than 80° C., for a time less than 1 hour, until reaching a concentration of carotenoids in the range between 10 and 40 g/l.

13. A process according to claim 1, wherein the extract enriched in carotenoids is subjected to a stage (7) of precipitation-crystallization through the addition of an alcohol, in the proportion 1/1 to 6/1 with respect to the volume of the solvent after the concentration (6) at a crystallization temperature less than 25° C. and for a crystallization time that ranges from 15 minutes to 24 hours.

14. A process according to claim 2, wherein soy lecithin is added at a percentage of 0.5-5%.

15. A process according to claim 2, wherein soy lecithin is added at a percentage of 0.5-1.5%.

16. A process according to claim 3, wherein the alcohol is methanol, ethanol, propanol or isopropanol.

17. A process according to claim 10, wherein the extract rich in carotenoids has a content of carotenoids greater than 90%.

18. A process according to claim 10, wherein the extract rich in carotenoids has a content of carotenoids greater than 95%.

19. A process according to claim 11, wherein the solvent used in the extraction stage (5) consists of an ethyl, propyl, isopropyl, butyl or isobutyl acetate or mixtures thereof.

20. The process according to claim 1, wherein the presence of the lecithin in the culture medium combined with the adjustment of pH results in the resultant level of gamma-carotene with respect to beta-carotene in the culture medium being 2.1%.

* * * * *